United States Patent [19]

Lacey

[11] Patent Number: 4,802,102
[45] Date of Patent: Jan. 31, 1989

[54] BASELINE CORRECTION FOR CHROMATOGRAPHY

[75] Inventor: Richard F. Lacey, Palo Alto, Calif.

[73] Assignee: Hewlett-Packard Company, Palo Alto, Calif.

[21] Appl. No.: 73,609

[22] Filed: Jul. 15, 1987

[51] Int. Cl.$^4$ ............... G06F 15/42; G01N 30/02
[52] U.S. Cl. ............... 364/497; 73/23.1; 364/498; 364/572; 364/571.02
[58] Field of Search ............ 364/497, 498, 571, 572, 364/733, 833; 73/23.1

[56] References Cited

U.S. PATENT DOCUMENTS

| | | | |
|---|---|---|---|
| 4,029,416 | 6/1973 | Hawes | 73/23.1 |
| 4,181,006 | 1/1980 | De Ford | 73/23.1 |
| 4,307,453 | 12/1981 | Kleiss | 364/571 |
| 4,314,343 | 2/1982 | Tomlinson | 364/498 |
| 4,338,811 | 7/1982 | Miyagi et al. | 364/498 |
| 4,357,668 | 11/1982 | Schwartz et al. | 364/497 |
| 4,455,084 | 6/1984 | Webb, Jr. et al. | 364/498 |
| 4,482,966 | 11/1984 | Mito et al. | 364/498 |
| 4,642,778 | 2/1987 | Hieftje et al. | 364/497 |
| 4,658,367 | 4/1987 | Potter | 364/572 |
| 4,660,151 | 4/1987 | Chipman et al. | 364/498 |

Primary Examiner—Parshotam S. Lall
Assistant Examiner—Kevin J. Teska

[57] ABSTRACT

Peak detection for a chromatogram is improved by removing systematic errors in the chromatogram using orthogonal subtraction. Orthogonal substraction involves subtracting from each spectrum in the chromatogram its expression in a spectral space representing the systematic errors. The data used in constructing the spectral space can be obtained in the form of spectra in the chromatogram occurring between component peaks. Principal component analysis can be applied to obtain a series of principal factors. A "hook method" can be applied to determine an optimum number of factors to use in constructing the spectral space, which is defined by the selected factors after normalization.

10 Claims, 3 Drawing Sheets

BASELINE CORRECTION FOR CHROMATOGRAPHY

BACKGROUND OF THE INVENTION

The present invention relates to chromatography and, more particularly, to a system and method providing for mathematical correction of systematic baseline errors in chromatograms.

While having a broad range of applications, the present invention arose in the context of liquid chromatography systems using ultraviolet and visible light spectral analysis in the generation of chromatograms. One challenge faced by such chromatography systems is that systematic errors in the spectra, introduced by solvents and other sources, interfere with analysis of peak shape and component identification. A major objective of the present invention is to provide a flexible mathematical method for minimizing the effects of such systematic errors in chromatographic analysis.

Liquid chromatography typically involves separation of the components of a sample mixture by movement of a solvent mobile phase over a solid stationary phase in a chromatograph column. Each mixture component is partitioned according to a characteristic "partition coefficient" between the phases, depending on the solvent or solvent mixture in the column at the time. As the mobile phase moves past the stationary phase, repeated adsorption and desorption of the component occurs at a rate determined chiefly by its ratio of distribution between the two phases. If the partition coefficients for the different mixture components are sufficiently different, the components exit the effluent end of the column in a series of bands which, theoretically, can be analyzed to determine the identity and original concentration of each mixture component.

A spectrometer can be used to analyze the eluting components by generating a chromatogram comprised of a series of spectra. Typically, a chromatogram is characterized by a series of peaks, each peak ideally representing a gradually rising and declining magnitude of a pure spectral component traceable to an individual mixture component. Theoretically, by comparing the detected spectra of a peak with known spectra for various compounds, the component can be identified. By integrating each identified component over its corresponding peaks, the relative concentrations of the components in the original mixture can be determined, at least in the ideal.

Inevitably, errors in the chromatogram adversely affect determination of component identity and concentration. Error can include both random and systematic errors, the present invention addressing the latter. Systematic errors include those with components which have a constant spectral shape but vary in magnitude, resembling the component spectra themselves in this regard. Most systematic errors however are characterized by wider temporal distribution than component peaks.

Systematic errors are introduced as a matter of course as raw spectral data reflect the spectra of one or more solvents of the mobile phase as well as the mixture components. There are additional sources of systematic errors, including changes in spectral absorbance due to temperature or other effects, variations in spectrometer lamp intensity and color, and variations in the spectrometer detector sensitivity.

Systematic errors due to solvent spectral absorbance are usually addressed by subtracting a spectral component attributed to one or more solvents from a chromatogram. This can be a relatively simple procedure where a single solvent is involved. However, more complex procedures use multiple solvents in time-varying ratios to accommodate complex mixtures with components having a wide range of solvent characteristics. In these more complex cases, "subtraction" involves subtracting the right components in the right concentrations at the right times.

In practice it is difficult to know what solvents are eluting in what concentrations at any given time. Irregularities in the pumping and mixing apparatus used to introduce solvent mixtures into the chromatographic column can create unintended transients and fluctuations prior to introduction. Some of these time-varying effects can be addressed by subtracting blank run chromatograms. The solvents can be run through a column without the mixture so as to produce a solvent chromatogram. The solvent chromatogram can be subtracted from the chromatogram of interest to the contribution of the solvents to the spectral data.

However, the blank run approach does not address other time-varying systematic errors or interactive effects between the solvents and the mixture components. The blank-run approach is costly in that a new blank run is required for each solvent set up. In fact, several blank runs are needed to place a confidence level on the solvent chromatogram, since variations can occur from run to run. These variations constrain the extent to which blank run subtraction can address systematic errors in a chromatogram. In practice, even after correction by current methods, significant systematic errors remain in chromatographic data, especially when complex solvent systems are involved.

Another problem in determining the identity and relative concentrations of mixture components concerns the inability of a given solvent system to separate all mixture components. For example, if two or more mixture components have nearly the same partition coefficient between the mobile and stationary phases, they tend to elute at about the same time. The result is that the corresponding component peaks overlap.

The problem with overlap can be addressed mathematically. Simple mathematical peak-shape tests permit identification of chromatogram features representing overlapping component peaks. More complex mathematical procedures can be used to deconvolve overlapping peaks so that the identity and relative concentrations of the overlapping components can be determined.

The mathematical procedures used in peak-shape tests and deconvolution are highly sensitive to systematic errors. As chromatography is applied to increasingly complex mixtures, it becomes increasingly difficult to resolve all mixture components chemically. Accordingly, it is becoming increasingly important to remove systematic errors from chromatographic data so that mathematical methods can supplement more effectively the spectral analysis of mixtures.

SUMMARY OF THE INVENTION

In accordance with the present invention, systematic errors can be removed from a chromatogram by replacing its spectra with their components orthogonal to a spectral space representing the systematic errors. This method involving orthogonal subtraction can be used subsequent to or in place of "blank subtraction" or other grosser attempts to remove systematic errors from a chromatogram.

The present invention requires the generation of a spectral space from spectra representative of systematic errors in a given chromatogram. In most cases, this data can be obtained by sampling a chromatogram between component peaks. The selection of appropriate samples can be done visually by choosing various points removed from each other and from significant peaks. More reliable mathematical methods are available, for example, based on the first and higher order time derivatives for the various spectra.

A spectral space can then be defined by the sample spectra so selected. The preferred method of constructing such a space involves principal component analysis. The sample spectra can be reexpressed as vector sums in a principal component space of orthogonal factors. Principal component analysis yields a set of vector components in decreasing order of significance in characterizing the sample data. Preferably a "hook" method or other algorithm is used to determine a suitable number of principal factors for characterizing the systematic error spectra. The selected principal factors define the spectral space used to remove systematic error from the given chromatogram.

Once the spectral space is determined, each spectrum of the original chromatogram is expressed in this space. From each original spectrum is subtracted its expression in the spectral space to yield a corresponding modified spectrum. This can be performed for all original spectra in the original chromatogram or any time interval thereof. The modified spectra so obtained then constitute a modified chromatogram.

With systematic errors thus removed, peak detection can be performed more reliably. Once a peak is reliably detected, the spectra constituting the peak can be added to provide a relatively error-free spectral component. This spectral component can be used for component identification by comparing this spectral component with standard spectra modified by subtraction of the standard spectrum in the same spectral space used to define the modified chromatogram. Alternatively, the modified component spectra can "resume" a more standard form by adding the orthogonal components subtracted in order to define the peak. Finally, mathematical peak-shape detection of overlapping component peaks and deconvolution can be applied with minimal distortion due to systematic errors.

The present invention has advantages over and above effective minimization of linearly additive systematic errors which are constant in shape but temporally varying in amplitude. While the spectra representing the systematic errors can be taken from a blank run or other source, this is avoidable. Systematic error spectra usually can be selected from between component peaks as well as at the beginning and end of a chromatographic run. Since blank runs are not required, many of the disadvantages associated with blank run methods are avoided, including the time and expense involved in blank runs. Additionally, errors due to inter-run variability are eliminated.

A related set of advantages flows from the fact that principal component analysis does not require prior knowledge of the sources of the systematic errors. Whereas prior procedures required knowledge and deliberate accommodation of each solvent system, the present invention automatically adapts to solvent system changes as reflected in the constructed spectral space. As a corollary, the present invention copes with systematic errors due to all sources, known or not, including temperature variations and spectrometer hardware related variations.

Accordingly, the present invention provides a system and method incorporating orthogonal subtraction and providing more effective minimization of systematic errors in chromatograms without prior blank runs or knowledge about the spectra representing the systematic errors. Other features and advantages of the present invention are apparent from the description below with reference to the following drawings.

DESCRIPTION OF THE PREFERRED EMBODIMENTS

Figure 1:
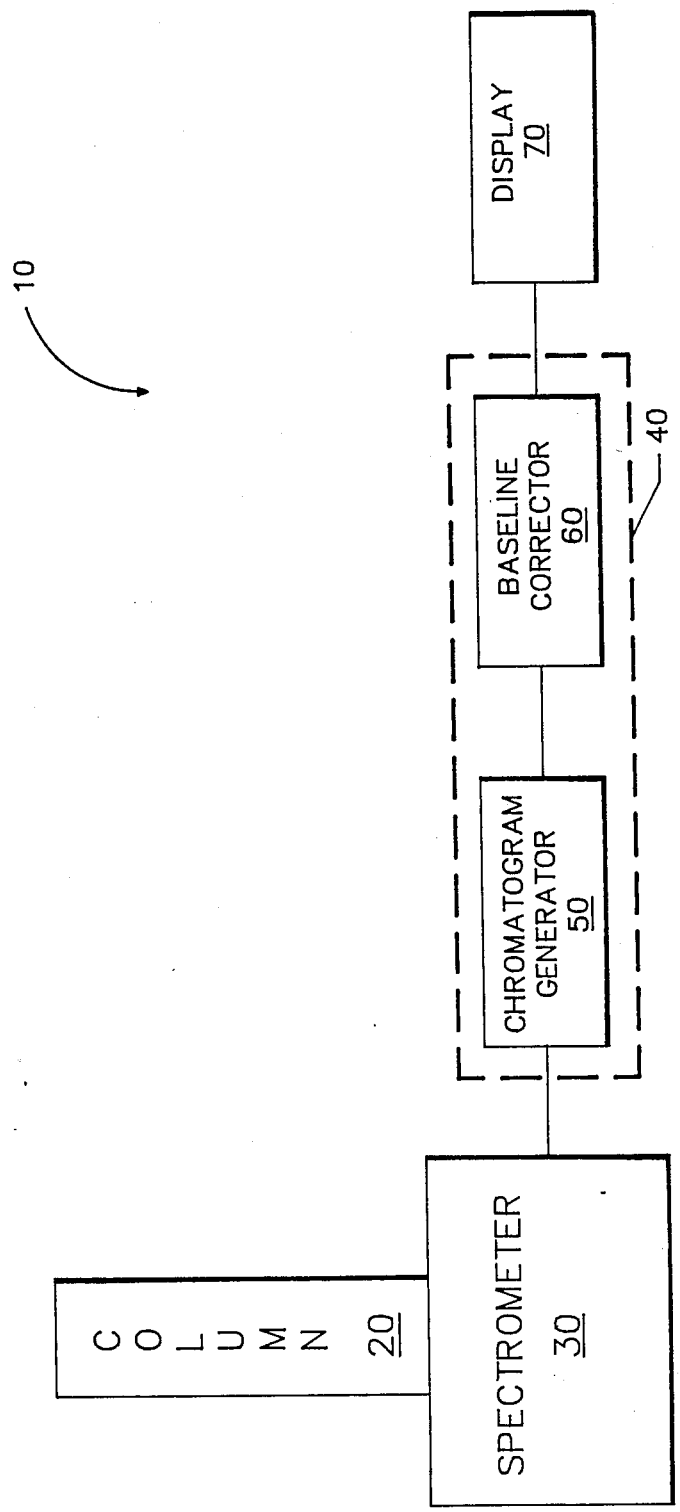
FIG. 1 is a chromatography system in accordance with the present invention.

A chromatography system 10 in accordance with the present invention comprises a chromatograph column 20, a spectrometer 30, a computer 40 including a chromatogram generator 50 and a base-line correction module 60, and a display 70. A sample mixture is introduced into the spectrometer 30 by means of a mobile phase carrier. The output of the spectrometer 30 is a series of spectra which are collected, stored and processed by the computer 40.

Figure 2:
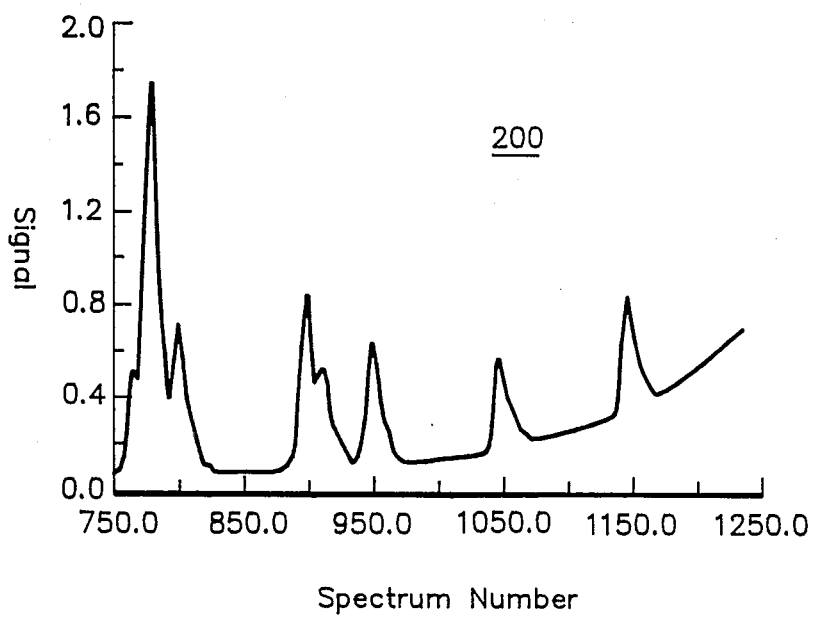
FIG. 2 is a chromatogram produced by the system of FIG. 1 prior to base-line correction.

The chromatogram generator 50 organizes the data into a chromatogram, without base-line correction in accordance with the present invention. The chromatogram 200 of FIG. 2 is a graphic representation of chromatographic data organized by the chromatogram generator 50. After base-line correction, the chromatographic data takes the form of chromatogram 300 of FIG. 3. Chromatograms 200 and 300 represent wavelength-averaged temporal sections of more extended experimentally obtained chromatograms.

Chromatogram 200 includes primary peaks around spectrum numbers j=780, 890, 940, 1040, and 1140. The primary peak at 780 appears to overlap secondary peaks, at about 760 and 800, to either side. The primary peak at 890 appears to overlap a secondary peak at about 910. Less resolved features at 950 and 1050 appear to follow the primary peaks at 940 and 1040. The regions around spectra 850, 1000, 1100, 1150 appear to be appropriate candidates for spectra representing solvent spectra and spectra for other systematic errors rather than component spectra of interest. These regions can be identified visually, or using mathematical algorithms which, for example, examine the first and higher order derivatives of the chromatogram 200. In the present case, individual spectrum numbers 830, 835, 975, 980, 1080, 1095, 1100, 1105, 1170, 1175, 1180, 1225 and 1230 are used to represent systematic errors.

Alternatively, clusters of spectra, rather than individual spectra can be used to generate the spectral space. Adjacent spectra can be clustered, and cluster averages used in the principal component analysis. This allows more data to be used and reduces the effects of random variations in individual spectra.

Figure 4:
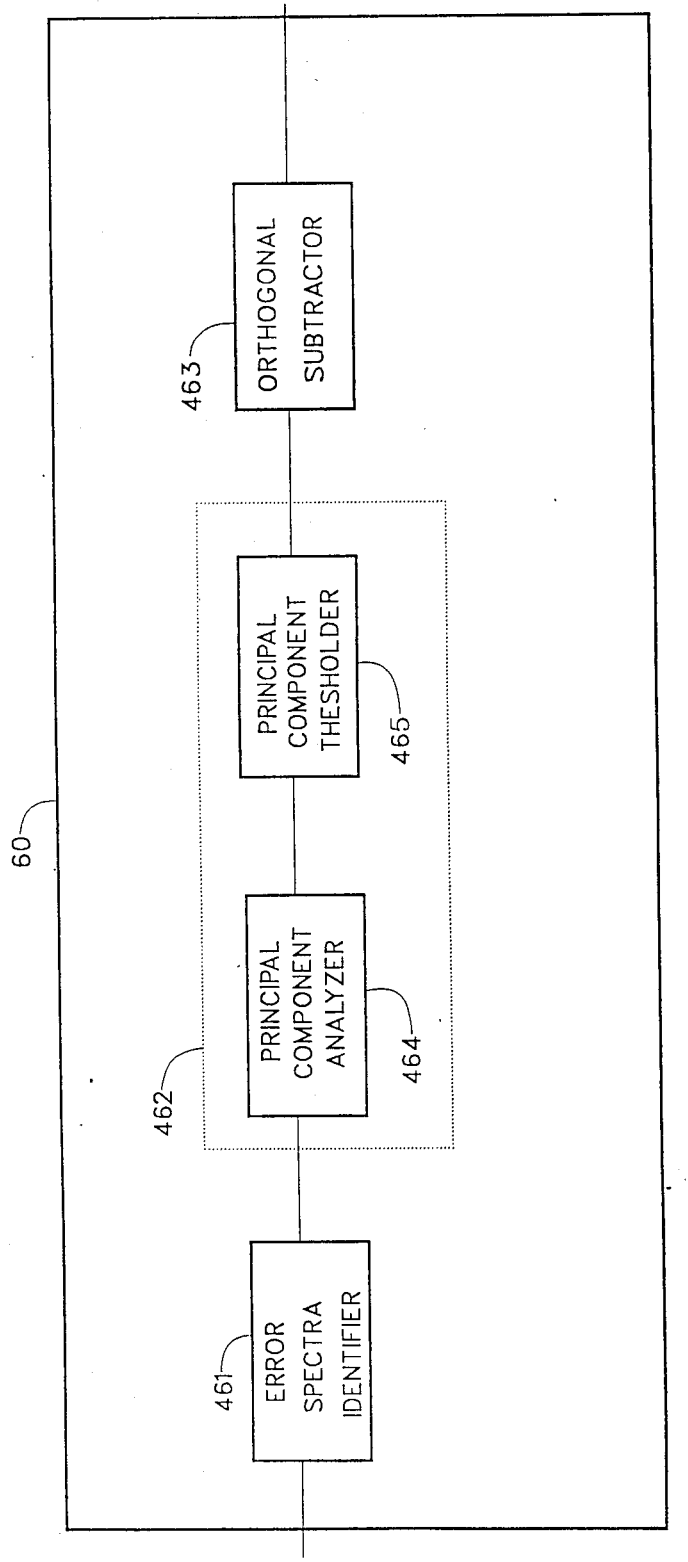
FIG. 4 is a detailed block diagram of a base-line correction module of the system of FIG. 1.

The error spectra used to generate the spectral space are selected from the chromatogram received by base-line correction module 60 from chromatogram generator 50. This selection is performed by an error spectra identifier 461, shown in FIG. 4. A space is constructed of these error spectra by space constructor 462, of base-line correction module 60, as indicated in FIG. 4. Space constructor 462 includes a principal component analyzer 464 which determines a space of orthogonal components and a principal component thresholder which selects the principal ones of these orthogonal components, according to suitable threshold criteria, for further use in the chromatographic analysis. An orthogonal subtractor 463 of base-line correction module 60 performs the orthogonal subtraction of this space from each spectral component of interest to remove systematic errors therefrom. The resulting corrected spectra are directed to display 70 of FIG. 1.

Each systematic error spectrum $R_e(j)$ is a vector representing a series of absorbance intensities $R_e(k,j)$ at each of the spectral frequencies k in the range of the spectrometer 30. These can be arranged into a matrix $R_e$, the columns of which represent systematic error vectors $R_e(j)$, and the rows of which correspond to individual spectral frequencies. Principal component analysis of this matrix $R_e$ yields a series of principal factors $R_1, F_2, F_3, \ldots$ in order to declining importance in characterizing the vectors $R_e(j)$.

Each of the vectors $R_e(j)$ can be expressed as a linear sum of all the principal factors. Principal component analysis permits significant gains in computational efficiency at some cost in precision by permitting less significant factors to be dropped from further processing. Various algorithms are available for assigning a cutoff point in the principal factor series. A "hook method" selects $F_n$ as the last factor retained, when $F_n$ is the last $F_k$ for which $\sigma_k/\sigma_{k-1} > 3$, where $\sigma_k$ is the singular value corresponding to the vector $F_k$. The chromatogram of FIG. 3 resulted from the use of three principal factors.

Alternative mathematical criteria are available. Other methods include assigning a fixed number of principal factors, e.g., 3, or equating the number of principal factors with the number of solvents or number of suspected major sources of systematic error. Another approach is to carry out the method of the present invention, first using one principal factor, and reiterating while incrementing the number of principal factors until the results converge, i.e., the baseline is substantially eliminated.

An orthonormal set of vectors $G_k$ is then constructed according to the equation $G_k = F_k/\sigma_k$. With respect to chromatogram 200, orthonormal vectors $G_1$, $G_2$, $G_3$ define a spectral space G. Alternatively, a spectral space of orthonormal vectors can be obtained in other ways. For example, a spectral space can be derived from the known spectra of the solvents by Gram-Schmidt orthogonalization.

Once the spectral space G is determined, each spectrum R(j) of chromatogram 200 can be expressed in that space as follows:

$$Q(j) = \Sigma_k(R'(j)G(k))G(k)$$

where R'(j) is the transpose of R(j).

Figure 3:
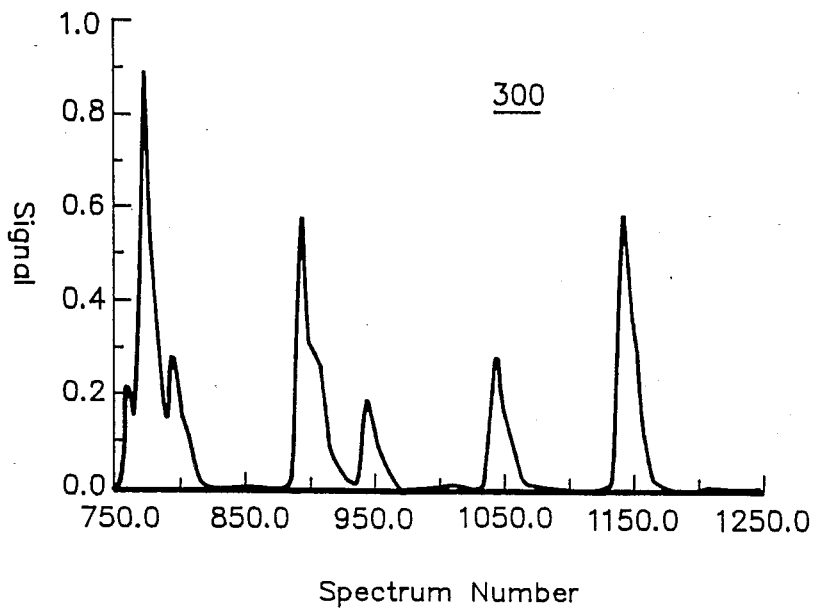
FIG. 3 is the chromatogram of FIG. 2 as modified by base-line correction in accordance with the present invention.

The spectra S(j) of chromatogram 300 of FIG. 3 can then be obtained by subtracting from each R(j) its expression in the spectral space G of systematic errors. This orthonormal subtraction can be expressed as $S(j) = R(j) - Q(j)$, where the vectors S(j) constitute a matrix S, which is represented by chromatogram 300 of FIG. 3.

Matrix S provides a sounder basis for peak detection than does the matrix R corresponding to chromatogram 200. Peaks can be detected from a plot of successive values of S(j), the magnitudes of vectors S(j), over a range of j's. Comparison of chromatograms 300 and 200 indicate the advantages of orthonormal substraction in delimiting peaks. For example, the primary peaks at 890 and 940 are better resolved relative to each other. In other words, one can determine more readily where the peak centered at 890 ends and the peak center at 940 begins. Furthermore, the boundaries of the primary peaks at 1040 and 1140 are much more clearly defined.

The minor peak preceding the primary peak centered at 780 is more clearly defined. Mathematical deconvolution now can be applied more successfully to determine the overlapping component spectra represented by spectra numbers 755–825. A peak-purity test can be applied to the remaining peaks to determine whether deconvolution is required elsewhere. Performing deconvolution using the modified spectra S(j) minimizes the likelihood that a solvent might appear as a spurious mixture component.

To the extent that the pure component spectra for the sample mixture are orthogonal to the spectra for systematic noise, the modified spectra correspond to the real spectra for the mixture components. Peak identification can be performed by correlating one of the spectra S(j) with spectra for known compounds. Preferably, several S(j) are averaged within a peak to improve signal-to-noise ratio before comparison.

More generally, orthonormal subtraction using spectral space G can be applied to standard spectra prior to correlation with the empirically determined spectra to aid in component identification. Alternatively, the standard spectra can be compared unmodified with the spectrum of a chromatographically isolated spectrum obtained by summing over index j over a peak: $\Sigma(S(j) + Q(j))$. This restores the original form of the peak, while taking advantage of the reduced systematic noise in defining the peak. Where mathematical deconvolution is applied, the estimated spectra of the pure components are linear combinations of the original spectra R(j), which can be reconstructed from the corresponding modified spectra S(j) and the orthonormal minuends Q(j) as in the case of isolated component peaks.

The present invention provides for many modifications of the foregoing embodiments. A systematic error spectral space can be constructed from known solvent or other spectra, or from blank runs or from a current run, or some combination of the foregoing. Where current or blank runs are used, there are alternative approaches to selecting representative spectra. Several approaches can be used to construct a spectral space from data, including principal component analysis and Gram-Schmidt orthogonalization. Clustered or unclustered spectra can be used in these constructions. The dimensionality of the spectral space can be predetermined or determined using various criteria. In addition, there are methods which differ in form from, but are mathematically equivalent to, the described methods. These and other modifications and variations are provided by the present invention, the scope of which is limited only by the following claims.

What is claimed is:

1. A system comprising:
spectra means for generating a series of spectra, each spectrum in said series being constituted by plural data values taken at different wavelengths and a common respective time;
orthonormal error space construction means for constructing an orthonormal spectral space from said series, said spectral space representing systematic errors in said series; and
orthonormal subtraction means for subtracting from each spectrum in said series a projection of the same spectrum in said spectral space.

2. The system of claim 1 wherein said series of spectra constitute a chromatogram.

3. The system of claim 2 further comprising identifier means for identifying systematic error spectra of said chromatogram representing systematic errors in said chromatogram, said identifier means being coupled to said spectra means for receiving a series of spectra therefrom, said identifier means being coupled to said constructions means so that said orthonormal spectral space can be constructed from a set of spectra representing systematic errors in said series of spectra.

4. The system of claim 3 wherein said construction means includes principal component means for performing principal component analysis on said systematic error spectra.

5. The system of claim 4 wherein said principal component means includes threshold means for determining a suitable number of principal components to be used in constructing said spectral space.

6. A method comprising:
generating a chromatogram having a series of spectra, each spectrum in said series being constituted by plural data values corresponding to different wavelengths and a common respective time;
constructing a spectral space representing systematic errors in said chromatogram; and
subtracting from each spectrum in said chromatogram a projection of that spectrum in said spectral space.

7. The method of claim 6 wherein said constructing step includes a substep of identifying systematic error spectra of said chromatogram, said systematic error spectra representing systematic errors in said chromatogram.

8. The method of claim 7 wherein said constructing step includes a subset of performing principal component analysis on said systematic error spectra.

9. The method of claim 8 wherein said constructing step includes a substep of determining a suitable number of principal components to be used in constructing said spectral space.

10. A method of characterizing a composition represented in a time-evolving eluent, said method comprising the steps of:
eluting said composition;
spectrally analyzing said evolving eluent to obtain a chromatogram having a series of spectra, each spectrum in said series being constituted by plural data values taken at different wavelengths and a common respective time;
selecting error spectra by selecting spectra of said series substantially devoid of contributions from said composition so that said error spectra represent systematic errors in said chromatogram;
constructing a spectral space from said error spectra by determining orthogonal principle components of said error spectra; and
subtracting from each spectrum of interest in said series a projection of that spectrum in said spectral space so as to obtain a corrected chromatogram substantially free of said systematic errors.

* * * * *